(12) United States Patent
Duplessie et al.

(10) Patent No.: US 6,375,639 B1
(45) Date of Patent: Apr. 23, 2002

(54) INTRAVENOUS STABILIZING DEVICE

(76) Inventors: Renee F. Duplessie; David S. Miller, both of 7211 Angela, Glendale, AZ (US) 85308

( * ) Notice: Subject to any disclaimer, the term of this patent is extended or adjusted under 35 U.S.C. 154(b) by 0 days.

(21) Appl. No.: 09/169,251

(22) Filed: Oct. 9, 1998

(51) Int. Cl.[7] ................................................. A61M 5/32
(52) U.S. Cl. ................... 604/174; 602/42; 128/DIG. 26
(58) Field of Search ................. 604/174–175, 604/177–180, 305, 307–8, 351–52, 327, 337, 345; 128/DIG. 26, 889; 602/54, 56, 42, 58, 60, 57; 606/213–16

(56) References Cited

U.S. PATENT DOCUMENTS

| | | | |
|---|---|---|---|
| 3,990,454 A | * 11/1976 | Schlesinger | 604/180 |
| 4,316,461 A | 2/1982 | Marais et al. | 128/214 R |
| 4,445,894 A | 5/1984 | Kovacs | 604/179 |
| 4,449,975 A | * 5/1984 | Perry | 604/179 |
| 4,490,141 A | * 12/1984 | Lacko et al. | 604/180 |
| 4,591,356 A | 5/1986 | Christie | 604/179 |
| 4,669,458 A | * 6/1987 | Abraham et al. | 128/133 |
| 4,737,143 A | 4/1988 | Russell | 604/180 |
| 4,799,923 A | 1/1989 | Campbell | 604/179 |
| 4,966,590 A | * 10/1990 | Kalt | 604/180 |
| 5,188,608 A | 2/1993 | Fritts | 604/179 |
| 5,294,312 A | * 3/1994 | Delk et al. | 604/180 |
| 5,306,256 A | 4/1994 | Jose | 604/180 |
| 5,342,317 A | 8/1994 | Claywell | 604/179 |
| 5,372,589 A | * 12/1994 | Davis | 604/180 |
| 5,389,092 A | * 2/1995 | Guillemet et al. | 604/304 |
| 5,445,604 A | * 8/1995 | Lang | 602/47 |
| 5,468,229 A | 11/1995 | Chandler | 604/179 |
| 5,549,567 A | 8/1996 | Wolman | 604/179 |
| 6,124,521 A | * 9/2000 | Roberts | 602/54 |

* cited by examiner

*Primary Examiner*—Angela D. Sykes
*Assistant Examiner*—Patricia Bianco
(74) *Attorney, Agent, or Firm*—Rader, Fishman & Grauer, PLLC

(57) ABSTRACT

A stabilizing device (20) for securing an intravenous catheter (22) to a patient's body is disclosed having a main body (24) with an opening (26) to allow passage of the catheter. The main body (24) includes a front portion (28) connected to a rear portion (30) by a pair of side portions (32). At least one of the side portions (32) has a slit (34) to enable the opening (26) to be placed around a previously installed catheter. A plurality of straps (36) are provided to wrap around the affected body portion of a patient. Loops (38), in the shape of a partial figure eight, are used to hold catheter tubing (22) to the main body (24) to prevent unwanted removal of the catheter.

17 Claims, 3 Drawing Sheets

INTRAVENOUS STABILIZING DEVICE

FIELD OF THE INVENTION

The present invention relates to a stabilizing device for catheters, and in particular, to intravenous catheters. The stabilizing device of the present invention includes a main body having an opening or window adjacent a needle insertion site and either a plurality of straps to attach the device to a patient's body or being of a wide band encircling the limb or appendage. Smaller narrow portions (loops) attached to, or extend from the main body of the device to secure the IV catheter tubing. The present invention eliminates the need for applying tape directly to the patient's skin.

BACKGROUND OF THE INVENTION

Many of the patients that enter a hospital are given an intravenous (IV) catheter for venous access as well as for the administration of fluids, medications, and parenteral nutrition. In the past, it has been common practice to apply tape directly to securely attach the catheter hub and tubing to the patient. However, certain patients have severe allergy to tape/adhesives. Furthermore, elderly, newborn and burn patients have frail or damaged skin that is not conducive to the use of tape to anchor an IV. In some instances, skin is actually removed when the tape is removed.

Previously, some designs have been proposed to alleviate the problem of direct taping. One such design utilizes a stabilizing sleeve having an outer fabric layer with a gauze inner layer that wraps around a patient's appendage and holds the IV needle and tube against the patient's appendage. The sleeve utilizes VELCRO adjacent a seam to removably fasten the sleeve to the appendage. Disadvantages to this are the potential for a tourniquet effect and the inability to view the area proximal to the IV site, not to mention the difficulty and cost in manufacturing it.

Another previously proposed design utilizes bands that wrap around a patient's appendage adjacent the insertion site of an IV catheter. Ends of the bands attach to each other using hook and loop type fasteners. Catheter tubing is anchored against the bands by using adhesive tape. Thus, the adhesive tape is applied to the bands and not the patient's skin. Some of the disadvantages to this design include: high cost manufacturing, increased risk of a tourniquet effect, inability to observe the sites proximal and distal to the IV catheter insertion site.

Yet another stabilizer design includes a base unit that is placed against the patient's body and includes wing straps having medical adhesive on one side which wrap around and attach to the base unit to secure the device to the patient. A low profile one-piece tub mount is centrally located in the base unit for grasping a tube.

However, none of the prior art of stabilizing devices have an opening or window to allow viewing of the area proximate the needle insertion site. In addition, the area proximal and distal to the insertion site is covered, therefore, prohibiting surveillance for IV infiltration. In addition, the prior designs lack the use of a disposable, resilient, surgical grade material that is self-adherent but non-adhesive to a patient's skin or hair. Also, the prior art lacks protection from a tourniquet effect because the materials are non-expansible.

SUMMARY OF THE INVENTION

The present invention is directed to a stabilizing device for securing a catheter to a patient's body at a catheter insertion site, the stabilizer device includes a main body for positioning over at least a portion of the catheter insertion site. An opening of sufficient size is formed in the main body for permitting passage of a catheter. Optionally, the opening is sized to permit viewing of an area f a patient's body distal the catheter insertion site. A slit is further formed in the main body and connected to the opening to allow the main body to be positioned around a previously installed catheter without requiring catheter removal. At least one attachment member is connected to the main body for securely attaching the stabilizing device to a patient. Optionally, but preferably, the main body is generally flexible for adapting to contours of a patient's body near the catheter insertion site. Therefore, the present invention reduces the amount of time for securing an IV catheter. Additionally, an existing catheter does not need to be removed when using the present invention, which reduces health risks and increases patient comfort.

Further, the present invention includes a stabilizing device for securing a catheter to a patient's body at a catheter insertion site, the stabilizer device including a main body for positioning over at least a portion of the catheter insertion site. An opening of sufficient size is formed in the main body for permitting passage of a catheter and at least one attachment member is connected to the main body for securely attaching the stabilizing device to a patient. Also, the main body and the at least one attachment member are formed from a self-adherent material that is non-adhesive. An example of a self-adherent material is one supplied by 3M Corporation under the trademark COBAN, which is disposable, resilient, extensible and surgical grade. Accordingly, the present invention is cost-effective and does not adhere to the patient's body.

Still further, the present invention includes a stabilizing device for securing a catheter to a patient's body at a catheter insertion site, the stabilizer device having a main body for positioning over at least a portion of the catheter insertion site. The main body includes a front strip connected to a rear strip by a pair of spaced apart side strips. An opening of sufficient size is formed in the main body for permitting passage of a catheter and at least one attachment member is connected to the main body for securely attaching the stabilizing device to a patient. Also, a slit is provided in the main body and connected to the opening to allow the main body to be positioned around a previously installed catheter without requiring catheter removal. At least one tubing fastener is selectively attachable to the main body for supporting a catheter tube. Moreover, each of the main body, the at least one attachment member, and the at least one tubing fastener are formed from a self-adherent material that is non-adhesive. In a preferred embodiment, the main body and the attachment member are formed integrally from one piece of self-adherent material. Optionally, the tubing fastener can be formed integrally with the main body and the attachment member.

Additionally, the present invention includes a stabilizing device for securing a catheter having a main body provided with an opening that allows passage of a catheter through it (or through a cut-out portion of a window). The main body further includes a front portion connected to a rear portion by a pair of side portions. At least one of the side portions has a slit to allow the opening to be placed around a previously installed catheter. Straps are connected to the side portions. At least one of the side portions extend outwardly away from the main body. These straps are used to attach the main body to a patient's appendage at a catheter needle insertion site. Loops, in the form of a partial figure eight shape, surround the catheter tubing and attach the tubing to the front and rear portions of the main body.

The present invention allows healthcare personnel to view the areas of a patient's body that are both proximal and distal to the needle insertion site to detect signs of complications such as IV catheter infiltration or phlebitis. The opening or window permits viewing of an area distal the needle insertion site, while the main body is configured to permit viewing of an area proximal the insertion site, for example, an area immediately above the front strip. Another feature of the present invention is the use of non-adhesive, disposable, self-adherent, surgical grade material for the entire device. Thus, the loops holding the tubing are pressed against the main body to attach the catheter in place. Then the straps can be wrapped around the affected appendage and can be applied over the ends of the loops to further hold the catheter in place. Further, the present invention is made of materials that have inherent extensibility that helps to prevent a tourniquet effect, if moderate swelling of the appendage occurs.

The present invention is directed to an IV stabilizing device which has a wide portion that encircles a limb or appendage with or without smaller narrow portions which secure the IV catheter to the device (not the patient). The wide portion is composed of a single wide band or smaller bands extending from a body (wide portion) to encircle the limb or appendage and connecting via self-adherence. There are many variations possible of this theme, not just the non-adhesive mechanisms illustrated in the figures. Obviously certain designs have advantages over other designs and will be more likely to become commercially used. The device may have the smaller narrow portions (loops) (which stabilize the IV catheter) either protruding into the central portion of the opening or window longitudinally, vertically, singularly, or plurally. The device may also have these smaller narrow portions (loops) protruding away from the body of the device (proximally and distally).

These narrow portions may either be connected to the device or integrally a part of the device. They may also be absent, with adhesive tape being used in their stead, as it will stabilize the IV catheter to the device instead of the patient.

The present invention is cost effective, easy to manufacture, and disposable to insure cleanliness. The present invention can be made of different width materials and therefore can be easily adapted to fit different size bodies and can be applied to different body sites (elbow, forearm, hand, leg, etc.) and is easily applied or removed by healthcare personnel, without the need to remove the IV catheter, by way of the slit and the opening formed in the main body. The device can and will likely be used in combination with a transparent, occlusive type dressing/bandage to maintain sterility of the catheter insertion site for use in patients where minimal adhesive use is not an issue. In patients where it is an issue, a sterile non-stick pad will be used in its stead.

The present invention can be used to stabilize many different types of catheters or similar devices including a percutaneous indwelling central catheter, also called a PICC line. A larger version can be used for stabilization of a central venous catheter cordis or Swan Ganz catheter by applying the stabilizing device in a figure 8 pattern about the shoulders and axilla, similar to a clavicular fracture splint/bandage.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION OF PREFERRED EMBODIMENTS

Figure 1:
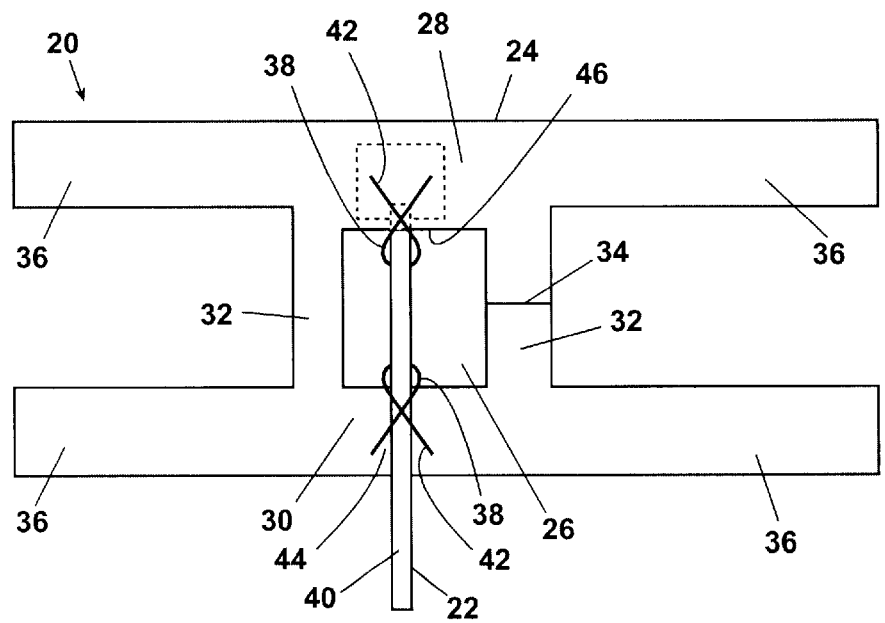
FIG. 1 is top view of a first embodiment of the present invention.

FIG. 1 shows a stabilizing device 20 for securing an intravenous (IV) catheter 22 to a patient's body (not shown). Stabilizing device 20 includes a main body 24 having a window or opening 26 to allow passage of IV catheter 22. Main body 24 further includes a front portion 28 connected to a rear portion 30 by a pair of side portions 32. At least one of the side portions 32 is provided with a slit 34 to enable window 26 to be placed around the previously installed catheter 22. Slit 34 can be selectively closeable to improve rigidity of stabilizing device 20.

A plurality of straps 36 are connected to side portions 32 and extend outwardly away from main body 24. Straps 36 are preferably integral with main body 24 and made of a same extensible surgical grade material. If a non-extensible surgical grade material is to be used, then elastic connections 80 may be incorporated to prevent a tourniquet effect. If another material is used that is not self adherent, the portions requiring self-adherent qualities may require VELCRO or adhesive which would increase production costs, thereby malting a self-adherent material ideal. One preferred material for stabilizing device 20 is a disposable, self adherent, surgical grade material supplied by 3M Corporation under the trademark COBAN. Slight pressure applied to overlapping regions of this material causes the overlapping regions to become fastened together. However, the material does not adhere to hair or skin, eliminating the problems caused by using adhesive tape. COBAN is generally thin, flexible and conforms well to a patient's body. COBAN also has some degree of inherent extensibility which reduces the potential for a tourniquet effect if the affected body portion begins to swell. However, any suitable surgical grade material may also be used.

A plurality of loops 38 are attached to, or project internally or externally, from the main body 24 to wrap around and hold tubing 40 of catheter 22. More specifically, one loop 38 is attached to front portion 28 and a second loop 38 is attached to rear portion 30. Loops 38 preferably form a gamma shape or partial FIG. 8 shape to secure tubing 40 and prevent catheter 22 from being pulled out. Loops 38 can also be made from the same self adhering surgical grade material as main body 24 and straps 36. Therefore, loops 38 can easily be pressed into place to secure them to main body 24. Additionally, if straps 36 are sufficiently long, they can wrap around the affected region and also overlap ends 42 of loops 38 to further retain loops 38 in position.

As illustrated in FIG. 1, tube 40 rests upon an outer surface 44 of rear portion 30 and contacts an inner surface 46 of front portion 28. Front portion 28 covers the site where a needle (not shown) of catheter 22 is inserted. But, the areas of patient skin on either side of front portion 28 remain visible for observation of catheter related conditions by healthcare personnel. The distal area adjacent the site of insertion is able to be viewed through opening 26 and can also serve as an area for taking a patient's pulse or temperature. Likewise, the proximal area to the IV insertion site, i.e. above front portion 28 and away from opening 26, can be easily viewed as well. Viewing of the proximal and distal areas is important to detect signs of complications, including for example, IV catheter infiltration or phlebitis.

Figure 2:
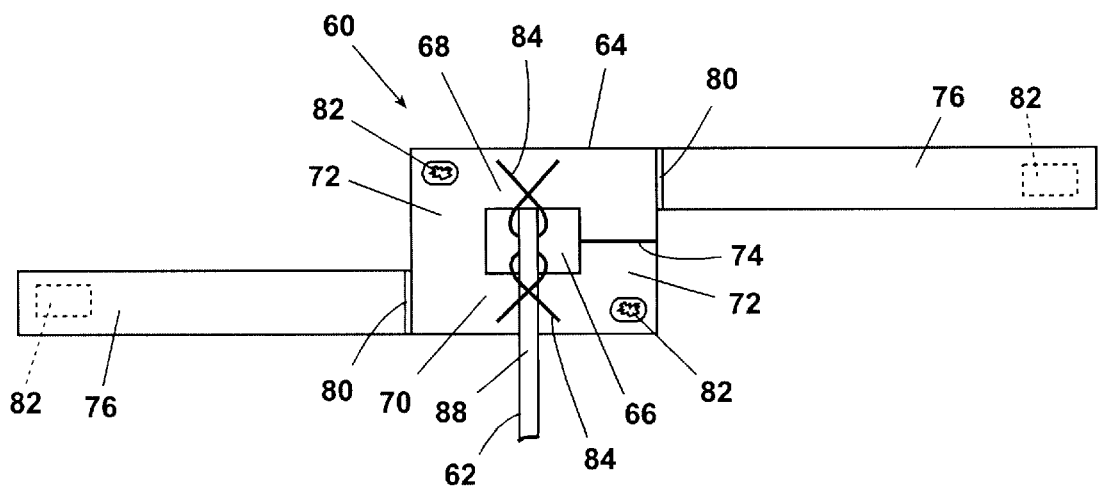
FIG. 2 is a top view of a second embodiment according to the present invention.

A second embodiment according to the present invention is shown in FIG. 2. Stabilizing device 60 includes a main body 64 having an opening 66 to allow passage of IV catheter 62. Main body 64 further includes a front portion 68 connected to a rear portion 70 by a pair of side portions 72. At least one of the side portions 72 is provided with a slit 74 to enable window 66 to be placed around the previously installed catheter 62.

A plurality of straps 76 are connected to side portions 72 and extend outwardly away from main body 64. Straps 76 are preferably made of a same surgical grade material as main body 64. Straps 76 can be attached to main body 64 using elastic 80 to provide resiliency. In addition, VELCRO patches 82 can be used to fasten the straps 76 to one another. Loops 84 made of tape can be attached to front and rear portions 68, 70 in a gamma shape or partial FIG. 8 shape, to retain tubing 88 against main body 64 in a somewhat rigid fashion. However, tape is only applied to the stabilizing device 60, not the skin.

Operation

The operation of the present invention is as follows. First, an IV catheter 22, 62 is inserted into a patient's vein and a sterile non-stick pad is applied to the needle insertion site. Next, slit 34, 74 is opened to allow main body 24, 64 to surround tubing 40, 88. After tubing 40, 88 is within opening 26, 66, slit 34, 74 is re-closed to prevent unwanted removal of stabilizing device 20, 60. Then, front portion 28, 68 is positioned so as to overlie the sterile pad. Optionally, this sterile non-stick pad can be incorporated in the construction of the overall device as an integral part of the device. Such a design would involve the opening being located in the bottom or distal aspect of the main body, instead of the proximal portion of the main body. Loops 38, 84 are formed into a partial figure eight shape around tubing 40, 88 with the ends of the loops being attached to the respective front and rear portions of main body 24, 64. Next, straps 36, 76 are wrapped around the affected body portion of the patient. As discussed above, the straps 36 are self-adhering and connect to the main body via localized pressure. Straps 76 can be connected using VELCRO.

Figure 3:
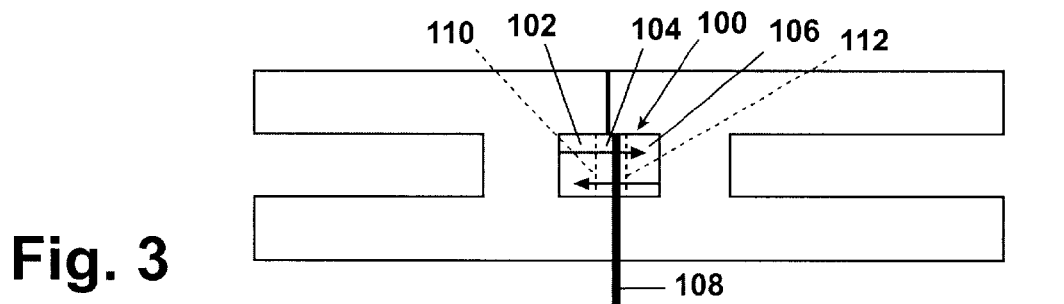
FIG. 3 is a top view of a third embodiment.

FIG. 3 shows a third embodiment of the present invention wherein a window or opening 100 is provided with a leftmost panel 102 connected to a middle panel 104 and a rightmost panel 106. Middle panel 104 is stationary and includes an opening to allow a catheter tube 108 to pass from one side of window 100 to the opposite side. Leftmost panel 102 and rightmost panel 106 are connected to middle panel 104 along fold lines 110, 112, and are able to be folded over on top of middle panel 104 to securely stabilize tube 108. After folding panels 102, 106 onto middle panel 104, window 100 is open on both sides of middle panel 104 to permit viewing of the area proximate the catheter insertion site.

Figure 4:
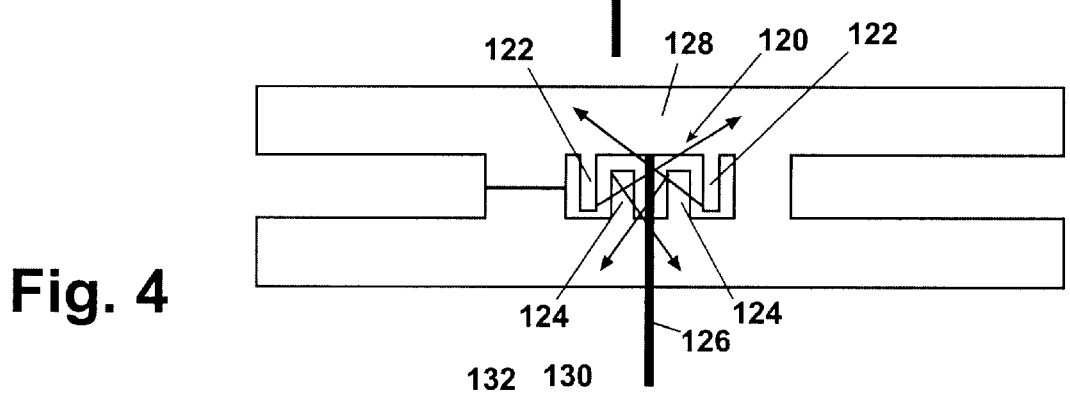
FIG. 4 is a top view of a fourth embodiment.

FIG. 4 shows a fourth embodiment of the present invention wherein a stabilizer device includes an opening or window 120 with a pair of upper tabs 122 and a pair of lower tabs 124 that can be integrally formed in opening 120. As indicated by the arrows, upper tabs 122 are pulled upwardly and crossed over each other in an "X" pattern underneath tube 126 and then fastened on top of main body 128. Lower tabs 124 are crossed over top of tube 126 as shown by the arrows and fastened to the main body 128 to achieve proper stabilization. Tabs 122, 124 are provided with sufficient length and positioned close enough to tube 126 to effectively wrap over the tube and be secured to the main body 128.

Figure 5:
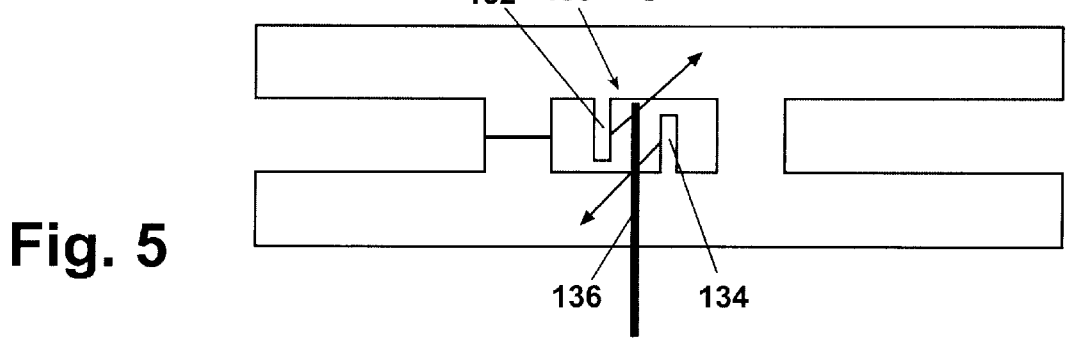
FIG. 5 is a top view of a further embodiment.

FIG. 5 shows a fifth embodiment of a stabilizer device wherein an opening or window 130 includes one upper tab 132 and one lower tab 134. Similar to the embodiment of FIG. 4, upper tab 132 travels diagonally under tube 136 and is attached onto main body 138 as indicated by the arrow. Lower tab 134 is folded diagonally back over top of tube 136 and is fastened to main body 138. Also, tabs 132, 134 are provided with sufficient length and positioned close enough to tube 126 to effectively wrap over the tube and be secured to the main body 128.

Figure 6:
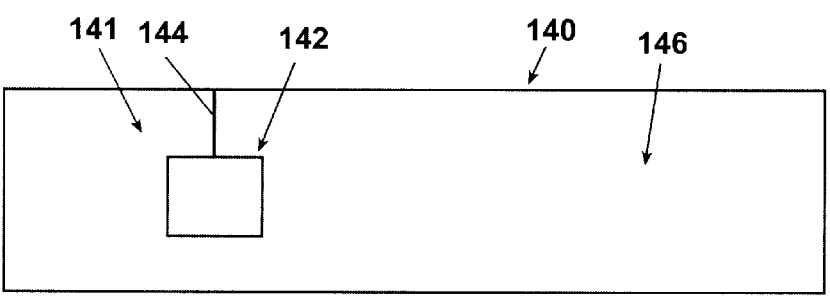
FIG. 6 is a top view of a sixth embodiment.
Figure 8:
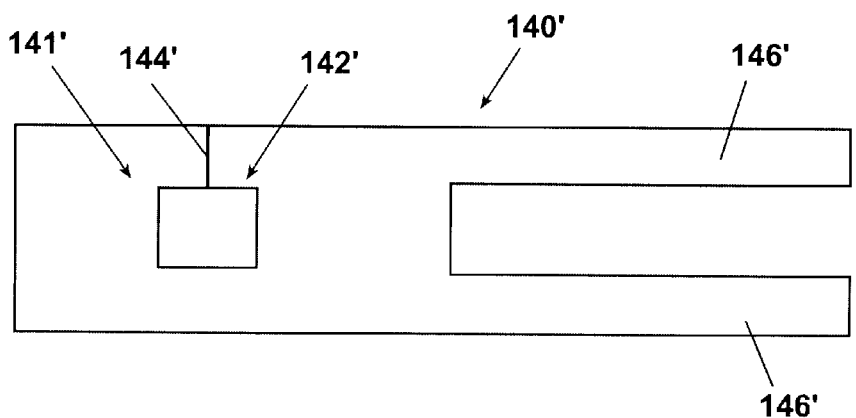
FIG. 8 is a top view of a still further embodiment.

FIG. 6 shows yet another embodiment of the present invention wherein a stabilizing device 140 is made from a single strip of material and has a main body portion 141 including an opening or window 142 and a slit 144 that allows installation around a tube (not shown). The strip can be a self adherent material or have separate fastening devices attached thereto. The strip includes a strap portion 146 which has sufficient length to encircle a patient's body at the insertion site. Although strap portion 146 is shown as the same width as main body portion 141, it is contemplated that strap portion 146 can be one or more narrow members extending outwardly from main body portion 141 at any location. For example, instead of being a single horizontal member, strap portion 146 can be a pair of vertically spaced apart narrow members 146' that extend horizontally from one side of a main body portion 141', as shown in FIG. 8. Corresponding elements are labeled as primed numbers.

Figure 7:
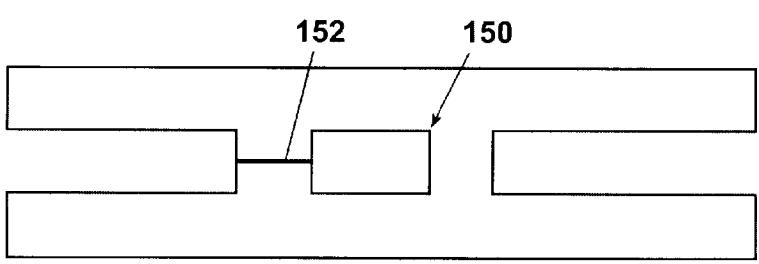
FIG. 7 is a top view of a further embodiment of the present invention.

FIG. 7 shows a still further embodiment according to the present invention, wherein an opening or window 150 is provided with a slit 152 and can be used to stabilize a catheter tube without additional loops or tabs.

Figure 9:
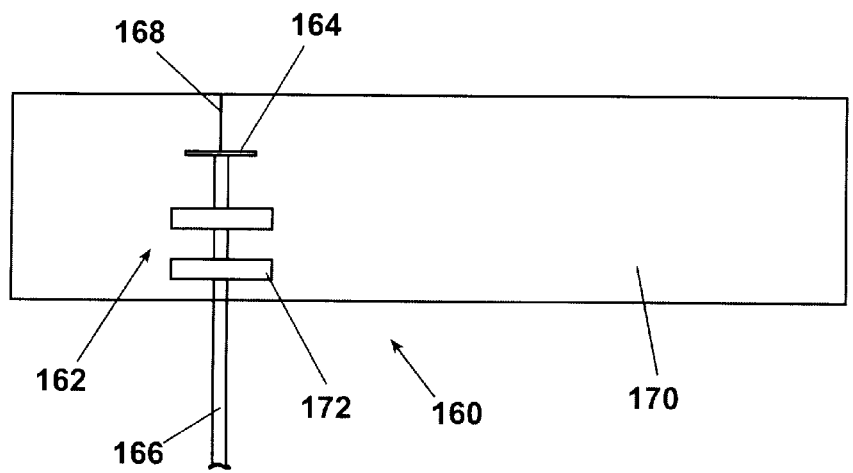
FIG. 9 is a top view of another embodiment according to the present invention.

FIG. 9 illustrates another embodiment of the present invention. A stabilizing device 160 is illustrated as being formed as a single strip of material and has a main body portion 162 including an opening 164 having sufficient size for allowing passage of a catheter tube 166. Unlike the previous embodiments, the present opening 164 is not sized to permit viewing an area of the patient's body that is distal to the catheter insertion site. Instead, opening 164 is sized only to permit acceptable passage of a catheter. In fact, opening 164 may be a single cut in the main body 162. A slit 168 extends to opening 164 from an outer edge of main body portion 162 and allows installation of stabilizing device 160 around a previously installed tube. Slit 168 can be selectively closeable to improve catheter retention. The strip of material can be a self adherent material or have separate fastening devices attached thereto, as described previously. The stabilizing device 160 includes a strap portion 170 which has sufficient length to encircle a patient's body at the insertion site. Although strap portion 170 is shown having the same width as main body portion 162, it is contemplated that strap portion 170 can be one or more narrow members extending outwardly from main body portion 162 at any location. Optionally, but preferably, one or more tabs 172 are provided to securely attach catheter tube 166 to the stabilizing device 160. Moreover, tab 172 is preferably made of the same self adherent, non-adhesive material as main body 162 to facilitate attachment and removal of tabs 172.

Regarding the present invention, it is contemplated that any of the different opening or window embodiments discussed above can be used with any type of overall stabilizing device. For example, although window 120 in FIG. 4 is illustrated on a stabilizing device having four straps, it is able to be adapted to any of the other stabilizing devices such as in FIGS. 2 or 6.

Moreover, although the main body is illustrated in the Figures as being generally rectangular, any suitable shape can be used, including, for example, circular, triangular, or hexagonal. Furthermore, although one or more straps are shown extending from the main body, any suitable number of straps can be provided. Also, each strap can extend at any suitable angle relative to the main body, including horizontally, vertically or diagonally. Likewise, any number of slits can be provided at any suitable location on the stabilizer device for providing access to the opening or window without removing a previously installed catheter.

Preferred embodiments of the present invention have been disclosed. A person of ordinary skill in the art would realize, however, that certain modifications would come within the teachings of this invention. Therefore, the following claims should be studied to determine the true scope and content of the invention.

What is claimed is:

1. A stabilizing device for securing a catheter to a patient's body at a catheter insertion site, the stabilizer device comprising:
   a main body for positioning over the catheter insertion site such that said main body covers said catheter insertion site;
   an opening formed in said main body and being of sufficient size for permitting passage of a catheter therethrough, wherein said opening is of sufficient size to permit viewing an area of a patient's body distal to the catheter insertion site;
   a slit formed in said main body and connected to said opening to allow said main body to be positioned around a previously installed catheter without requiring catheter removal; and
   at least one attachment member formed from a self-adherent material that is extensible, said attachment member being connected to said main body for securely attaching said stabilizing device to a patient;
   wherein the main body and said at least one attachment member is non-adhesive to said patient's body.

2. The stabilizing device of claim 1, wherein said main body is generally flexible for adapting to contours of a patient's body near the catheter insertion site.

3. The stabilizing device of claim 1, wherein said main body includes a front portion connected to a rear portion by a pair of spaced apart side portions.

4. The stabilizing device of claim 3, wherein said slit is formed in one of said front, rear or side portions.

5. The stabilizing device of claim 3, wherein said front portion of said main body is adapted to cover the catheter insertion site to permit viewing of an area of a patient's body distal to the catheter insertion site.

6. The stabilizing device of claim 1, further including at least one tubing fastener for securely attaching a catheter tube to said stabilizing device.

7. The stabilizing device of claim 6, wherein said at least one tubing fastener is one of a loop or a tab that is selectively attachable to said main body for supporting a catheter tube.

8. The stabilizing device of claim 6, wherein said at least one tubing fastener is a panel connected to said main body and located proximate said opening for supporting a catheter tube.

9. A stabilizing device for securing a catheter to a patient's body at a catheter insertion site, the stabilizer device comprising:
   a main body for positioning over the catheter insertion site;
   an opening formed in said main body and being of sufficient size for permitting passage of a catheter therethrough;
   at least one attachment member connected to said main body for securely attaching said stabilizing device to a patient; and
   wherein both said main body and said at least one attachment member are formed from a homogeneous self-adherent material that is extensible;
   wherein the main body and said at least one attachment member is non-adhesive to said patient's body.

10. The stabilizing device of claim 9, wherein said main body and said at least one attachment member are formed integrally from a single piece of material.

11. The stabilizing device of claim 9, wherein said at least one attachment member is a strap.

12. The stabilizing device of claim 9, further including a slit formed in said main body and connected to said opening to allow said main body to be positioned around a previously installed catheter without requiring catheter removal.

13. The stabilizing device of claim 9, wherein said at least one attachment member is a single strap extending outwardly from said main body.

14. The stabilizing device of claim 9, wherein said at least one attachment member is a plurality of straps extending outwardly from said main body.

15. The stabilizing device of claim 9, further including at least one tubing fastener for securely attaching a catheter tube to said stabilizing device.

16. The stabilizing device of claim 15, wherein said at least one tubing fastener is formed from a same self adherent material as said main body and is selectively attachable to said main body for supporting a catheter tube.

17. A stabilizing device for securing a catheter to a patient's body at a catheter insertion site, the stabilizer device comprising:
   a main body for positioning over a catheter insertion site, said main body having a front strip connected to a rear strip by a pair of spaced apart side strips;
   an opening formed in said main body and being of sufficient size for permitting passage of a catheter;
   said main body being configured for permitting viewing of an area of a patient's body proximal to the catheter insertion site to observe catheter related conditions;
   at least one attachment member connected to said main body for securely attaching said stabilizing device to a patient;
   a slit formed in said main body and connected to said opening to allow said main body to be positioned around a previously installed catheter without requiring catheter removal;
   at least one tubing fastener selectively attachable to said main body for supporting a catheter tube; and
   wherein each of said main body, said at least one attachment member, and said at least one tubing fastener are formed from a self-adherent material that is non-adhesive to said patient's body.

* * * * *